United States Patent [19]

Yamamoto et al.

[11] Patent Number: 5,059,186
[45] Date of Patent: Oct. 22, 1991

[54] PERCUTANEOUS ACCESS DEVICE

[75] Inventors: Ronald K. Yamamoto, Atherton; Stanley R. Conston, San Carlos; Matthew Bootman, Redwood City, all of Calif.

[73] Assignee: Vitaphore Corporation, San Carlos, Calif.

[21] Appl. No.: 328,425

[22] Filed: Mar. 23, 1989

Related U.S. Application Data

[63] Continuation-in-part of Ser. No. 166,779, Mar. 7, 1988, abandoned, which is a continuation of Ser. No. 857,647, Apr. 29, 1986, abandoned.

[51] Int. Cl.$^5$ .............................................. A61M 25/01
[52] U.S. Cl. ................................. 604/280; 604/167; 604/265; 128/658
[58] Field of Search ............................... 604/164–169, 604/256, 280, 283, 265, 175, 905; 128/656, 658

[56] References Cited

U.S. PATENT DOCUMENTS

| | | | |
|---|---|---|---|
| 3,598,127 | 8/1971 | Wepsic | 604/265 |
| 3,699,956 | 10/1972 | Kitrilakis et al. | 604/265 |
| 3,739,778 | 6/1973 | Monestere, Jr. | |
| 3,797,478 | 3/1974 | Walsh | 604/256 |
| 3,921,631 | 11/1975 | Thompson | |
| 3,927,672 | 12/1975 | Garcia | |
| 4,000,739 | 1/1977 | Stevens | 604/167 |
| 4,149,535 | 4/1979 | Volder | 604/164 |
| 4,252,122 | 2/1981 | Halvorsen | 604/164 |
| 4,473,067 | 9/1984 | Schiff | |
| 4,475,548 | 10/1984 | Muto | 604/167 |
| 4,496,348 | 1/1985 | Genese et al. | 604/169 |
| 4,531,937 | 6/1985 | Yates | |
| 4,551,146 | 11/1985 | Rogers | 604/256 |
| 4,580,573 | 1/1985 | Quinn | 604/169 |
| 4,603,152 | 7/1986 | Lavrin et al. | 604/265 |
| 4,676,762 | 6/1987 | Yamamoto et al. | 604/175 |

Primary Examiner—Stephen C. Pellegrino
Attorney, Agent, or Firm—Heller, Ehrman, White & McAuliffe

[57] ABSTRACT

A percutaneous access device for aseptically introducing catheters or other tubes into the body, is disclosed. In one aspect, the device comprises a valve housing having a tapered inner bore; a tapered tubular valve means which is inserted into the valve housing bore and comprises one or two valves; and a valve cap which is screwed into the valve housing behind the valve. The valve means, housing and cap have bores along a common axis to permit the insertion of a tube such as a catheter through the device and into the body. The cap and valve housing cooperatively compress the valve means to selectively seal the valve bore about the catheter, close the valve bore when the catheter is removed, and provide anti-microbial wiping action of the catheter during insertion. The valve means may comprise two valves, a hemostatic sealing valve and an anti-bacterial squeegee valve which provides accelerated release of the anti-bacterial agent under mechanical compression. Alternatively, the two valves may comprise a first, convex hemispherical valve which provides an air reflux barrier and mechanical seal when the catheter is not present and a second, cylindrical valve compressed between the first valve and the locking cap for providing a compressively-enhanced long-term anti-bacterial mechanical sealing barrier when the cap is locked over the inserted catheter and anti-bacterial wiping action during insertion or removal of the catheter with the cap unlocked. In another alternative, the wiping/squeegee function and the sealing functions are cooperatively provided by a duck bill valve, and a cylindrical valve with an O-ring.

23 Claims, 5 Drawing Sheets

PERCUTANEOUS ACCESS DEVICE

This is a continuation-in-part of our U.S. patent application, Ser. No. 166,779, filed Mar. 7, 1988, entitled "Percutaneous Access Device", now abandoned, which is a continuation of our U.S. patent application, Ser. No. 857,647, filed Apr. 29, 1986, entitled "Percutaneous Access Device", now abandoned.

BACKGROUND OF THE INVENTION

The present invention relates to a percutaneous access device and, in particular, to a percutaneous access device having self-sealing and aseptic characteristics.

In the practice of medicine, it is frequently necessary to introduce catheters or other tubular devices into the body and either rotate, push in or pull out the device to adjust the position of the intracorporeal end during the therapeutic or diagnostic procedure. One example is the insertion of vascular access catheters within the heart to access its functional condition. Inherent to such procedure, however, is the risk of trauma to the tissue at the skin interface with the device, of bacterial contamination caused by introduction of the catheter from the non-sterile environment outside the body, and of leakage.

Valves are used in certain catheter applications to prevent leakage via back-flow or reflux. In certain medical applications such as the vascular access applications alluded to above, the valve function is critical to patient health. For example, in vascular access and, in particular, in the use of heart flow diagnostic and pacing catheters, a sheath introducer is used to access the vascular system. The required diagnostic catheter is then placed through the lumen of the sheath introducer into the desired position within the heart. The sheath introducer contains a valve through which the diagnostic catheter passes, and prevents blood from leaking out and air embolisms from entering the patient should the patient sit up quickly. The valve should ideally perform these prophylactic functions both with and without the intraluminal catheter in place. However, because a relatively large bore catheter must pass through the valve, the valve must have a large opening, making sealing of the valve more difficult. In addition, the valve must work at the relatively low pressures associated with vascular physiology.

In addition to fluid and gas sealing properties, the valve should ideally provide an aseptic seal. During repositioning of the catheter, increasing the internal length of the catheter forces a segment previously exposed to the environment and bacterially contaminated into the blood stream.

To our knowledge, previously, there has not been available a device of simple construction which provides effective sealing and resealing functions for vascular access nor, in particular, a device which combines effective sealing and resealing functions as well as anti-microbial and wiping functions.

SUMMARY OF THE INVENTION

In view of the above discussion, it is among the objects of the present invention to provide a percutaneous access device which introduces a tubular device such as a catheter into the body, seals about the tubular device during the introduction of the device and after the device is in position, and allows resealing upon removal of the tubular device.

It is a related object to provide such a device which also performs wiping or both wiping and anti-bacterial functions to prevent bacterial contamination caused by introducing the tubular device into the body from the external, non-sterile environment.

Another object is to provide such a percutaneous access device which allows for introduction, removal, rotation and other adjustment of the tubular device without trauma to the tissue at the skin interface.

It is still another object, not exhaustive, to provide a percutaneous access device which incorporates the above functions and characteristics, yet is of simple, easily fabricated design.

In one embodiment, our percutaneous access device which accomplishes the above and other objectives comprises a tubular valve housing or hub having an integral or removable intracorporeal tube at the inner or proximal end and a tapered, internal, axial bore; a flexible apertured valve or plug means the same size and configuration as the valve housing bore and tapered at opposite ends; and a valve cap which is compressively locked onto the valve housing bore behind and against the valve means, and has an axial bore which is tapered at the inner end.

Insertion of the valve cap into the bore behind the plug compresses the valve means between the valve cap and the mating tapered surfaces of the valve housing and cap and thereby constricts the valve means. This constriction provides a seal against the outside surface of an introduced tubular element, and seals the valve means aperture when the tubular element is withdrawn.

The valve means can be formed of a flexible, elastomeric anti-bacterial material which acts as a bacterial squeegee, wiping off and inactivating bacteria during the introduction and use of tubular elements, as well as providing the above-described sealing and resealing functions. Our percutaneous access device permits insertion, withdrawal and adjustment of tubular devices into the body without trauma to the tissue at the skin interface. Also, the intracorporeal tube may include a raised annulus of tissue growth promoting material for providing a tissue seal and mechanical attachment to the skin.

In another embodiment, the sealing and anti-bacterial wiping functions of our percutaneous access device are separated by using two valves which perform the respective functions. The hemostatic sealing can be provided by either a duck bill or diaphragm valve. The anti-bacterial action of the squeegee valve is enhanced by the compression exerted by the valve cap, which accelerates/increases the release of the anti-bacterial agent. The valve compression is exerted upon locking of the valve cap, usually just after catheter introduction or manipulation, providing an extra bolus release of anti-bacterial agent after a potentially contaminating movement of the catheter.

In another compressively recharged, two-valve embodiment, there is provided an axially outwardly-extending, transversely slit, hemispherical sealing valve which provides mechanical sealing against air reflux and liquid leakage when a catheter is not present. The second valve, which is positioned between the first valve and the valve cap, comprises a cylindrical valve body which is impregnated with the compressively rechargeable anti-bacterial agent and further includes an internal, radially inwardly-extending ring or protuberance. The ring acts to compressively engage the outer diameter of a tubular device such as a catheter positioned within the hub. This mechanically seals the catheter and also provides the bacterial squeegee/scraping action to remove bacteria from the catheter surface. Preferably, the valve cap and hub are designed to provide a fixed locking position of the valve on the hub which as a consequence limits compression of the catheter and prevents damage to the catheter.

DETAILED DESCRIPTION OF THE PREFERRED EMBODIMENTS

A. Single Valve Embodiments

Figure 1:
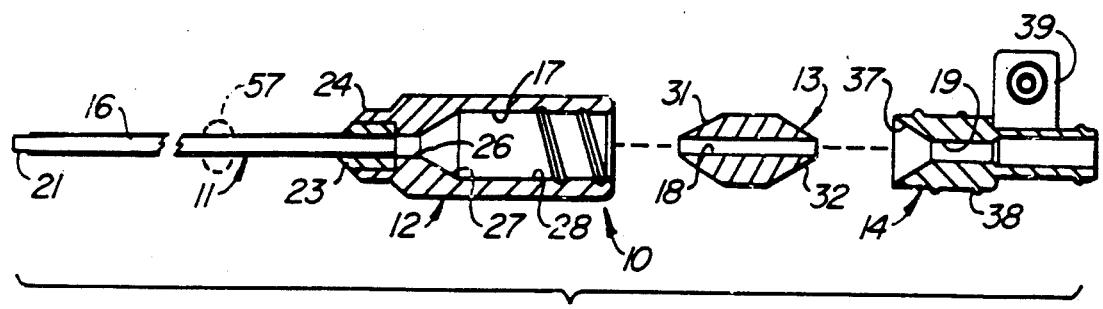
FIG. 1 is an exploded, longitudinal sectional view of a percutaneous access device with a single anti-bacterial valve which embodies the present invention.
Figure 2:
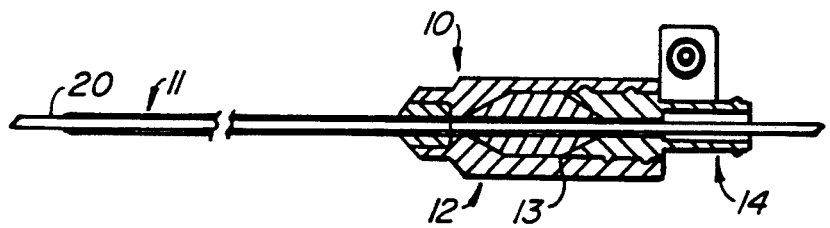
FIG. 2 is a longitudinal sectional view of the percutaneous access device of FIG. 1, as assembled, depicting insertion of a tubular device such as a catheter.
Figure 3:
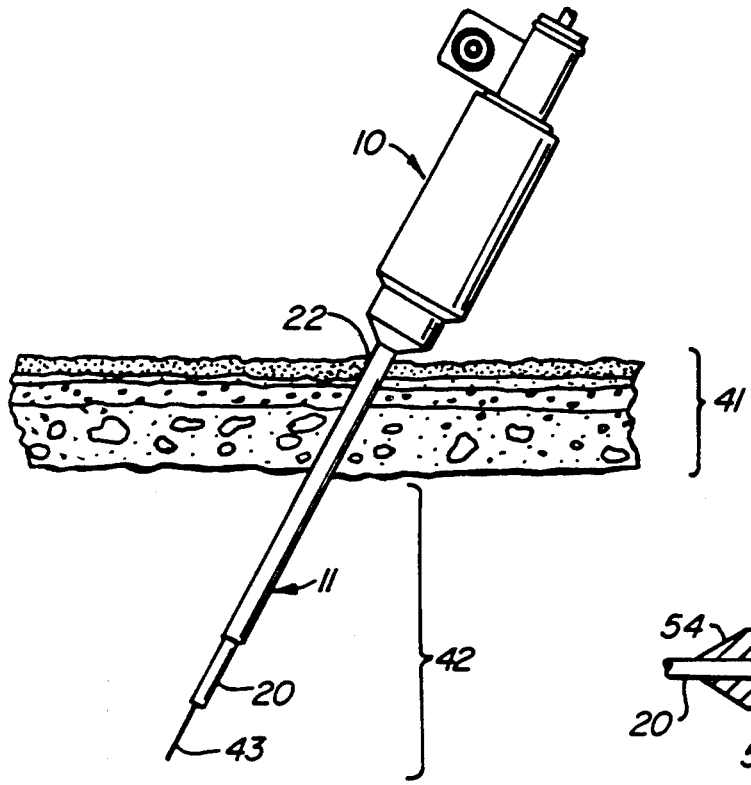
FIG. 3 depicts the use of the percutaneous access device of FIGS. and 2 in positioning a catheter within the body.

Referring to FIGS. 1-4 and, in particular, to FIG. 1, in one embodiment 10, our percutaneous access device comprises: an intracorporeal tube 11; a valve housing 12; valve or plug means 13; and valve cap 14. These components have communicating central bores therein, respectively designated 16, 17, 18 and 19, for permitting the insertion and removal of tubular elements or devices such as catheter 20 (FIGS. 2 and 3). Preferably, the introducer tube 11 has a tapered intracorporeal end 21 (FIG. which facilitates insertion of the device through a skin incision 22 (FIG. 3) into the body.

The diameters of the bores 16-19 can be chosen so that the percutaneous access device can be used to introduce a number of other elements such as electrical wires (which are used, e.g., for regulating and/or monitoring functions) and bone pins. Also, the introducer tube 11 can be formed integrally with valve housing 12 or can be formed as a separate component which is removable for replacement, sterilization, etc.

In the illustrated embodiment of FIG. 1, tube 11 includes a threaded male fitting at the outer or top end thereof for removable attachment to mating bore 24 in the inner or proximal end of the valve housing bore 17. (Please note, designations such as proximal and distal, inner and outer, bottom and top are used to indicate relative position only, not as a limitation.) From inner end section 24, the valve housing bore 17 is stepped to an adjacent small diameter section 26 having approximately the same diameter as tube bore 16, and expands via conical tapered section 27 to a relatively large diameter outer or distal section 28 which is threaded adjacent the outer end thereof.

In the embodiment of FIG. 1, valve means 13 comprises a single valve, sized and configured to precisely abut the tapered wall 27 and bore 28 of the valve housing 12. Specifically, the valve body is formed of a firm, yet flexible material and has a tapered conical proximal end 31 and a cylindrical body which precisely conform to the surfaces 27 and 28 of the valve housing bore 17. The opposite, or distal end 32 is also tapered. The valve bore or lumen 18 is approximately the same diameter as (typically slightly larger than) the tube bore 16.

The outer surface of the proximal end 38 of the tubular valve cap 14 is threaded for insertion into the threaded valve housing bore 17. The proximal end 37 of the bore 19 has a conical tapered section which mates with the tapered outer end 32 of valve 13. Flange 39 is used to rotate the valve cap for insertion into and removal from the distal end of the valve housing 12.

To assemble and use the percutaneous access device 10, initially, the tubular introducer 11 is secured to the front or proximal end of the valve housing 12, the tapered valve 13 is placed in the valve housing 12 and the valve cap 14 is screwed into the outer or distal end of the valve housing 12. Referring to FIG. 3, the assembled percutaneous access device 10 is now ready for introduction via the skin incision 22 through the skin 41 and into tissue 42 such as the vascular system. This introduction may be facilitated by the use of a guide wire 43.

Next, a catheter 20 or other tubular device is inserted into and through the percutaneous access device 10 and the flange 39 is tightened as needed to ensure antimicrobial wiping action as the catheter is advanced along guide wire 43 and into the tissue 42. After the insertion of the catheter, the valve cap 14 is tightened further against the tapered valve 13. Referring also to FIG. 2, in this position the valve cap surface 37 and the surface 27 of the valve housing bore cooperatively exert compressive force against the tapered valve 13. As a consequence of the presence of the mating tapered plug and valve housing surfaces, a controlled component of the compressive force is transmitted radially inwardly against the plug, thus constricting the bore 18 at both ends thereof and sealing the valve about the external surface of the catheter 20. (The catheter is also thus mechanically locked into a fixed intracorporeal length.)

To remove the device 20, valve cap 14 is unscrewed slightly to loosen the engagement of valve 13 against the device 20; the device is then withdrawn; and the valve cap may be tightened against the valve to reseal bore 18. Alternatively, an aggressive taper may be used (i.e., a smaller angle between valve surfaces 31 and 32 and the longitudinal device axis) and/or the valve 13 may be formed of a softer elastomer or other material, so that the cooperative coaction between the valve cap 14-valve 13-valve housing 12 provides an automatic resealing function. That is, the compressive force closes or reseals the bore 18 upon removal of the catheter, yet maintains a passageway into the body for later introduction of another tubular device, without (or with reduced) loosening and retightening the valve cap 14.

Finally, during removal of the catheter 20 and, in particular, during insertion or manipulation thereof, the compressive force on the bore 18 both wipes off and inactivates bacteria. That is, the valve 13 acts as an anti-bacterial squeegee.

In short, the tapered valve housing 12, the anti-bacterial, tapered valve or plug 13 and the threaded valve cap 14 cooperate to seal and reseal the plug during insertion and withdrawal of a tubular element, provide anti-bacterial wiping and inactivation of bacteria during insertion, and permit rotation and other adjustment of the tubular device without trauma to the skin at the interface.

Preferably, the tube 11, the valve housing 12 and the valve cap 14 are formed from thermoplastic polymers suitable for injection molding such as polyethylene, nylon, polyacetyl, teflon, polyurethane and polyvinyl chloride. The valve 13 is formed of flexible anti-bacterial elastomer material such as silicon rubber or urethane elastomers with an anti-bacterial agent such as antibiotics, chlorhexidine disinfectants, providone-iodine, quaternary ammonia compounds and "oligodynamic" silver and gold compounds.

FIG. 1 depicts, in phantom, an optional ring or annulus 57 which preferably is formed of skin ingrowth-promoting material and is mounted on the intracorporeal tube 11 for providing a tissue seal and mechanical attachment to the skin 41.

Figure 4:
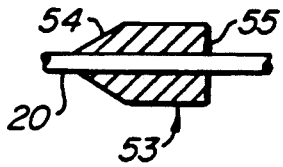
FIG. 4 depicts an alternative valve or plug which is tapered at one end.

FIG. 4 illustrates an alternative embodiment 53 of the valve or plug which is tapered only at the proximal end 54. Outer or distal end 55 is not tapered. Presently, double tapered valve 13, FIG. 1, is preferred for its sealing action at each end.

In another alternative embodiment, the valve 13 could be formed without a bore initially. The bore 18 could then be formed by inserting a puncturing device such as a needle into the percutaneous access device 10 and through the soft resilient material which forms the valve 13. In some applications, the valve puncturing device itself might be the element which is inserted into the body.

B. Two-Valve Embodiments

FIGS. 5-7 and 10-13, respectively, depict the construction and use of two, two-valve embodiments 60 and 100 of our percutaneous access device. Both devices are somewhat similar in construction and quite similar in use to the device 10, the primary exception being the two-valve construction. Thus, much of the discussion above regarding the construction and use of the device 10 applies to the devices 60 and 100 as well. The following discussion emphasizes the differences.

1. Device 60: Hemostatic Sealing Valve and Anti-Bacterial Squeegee Valve

Figure 7:
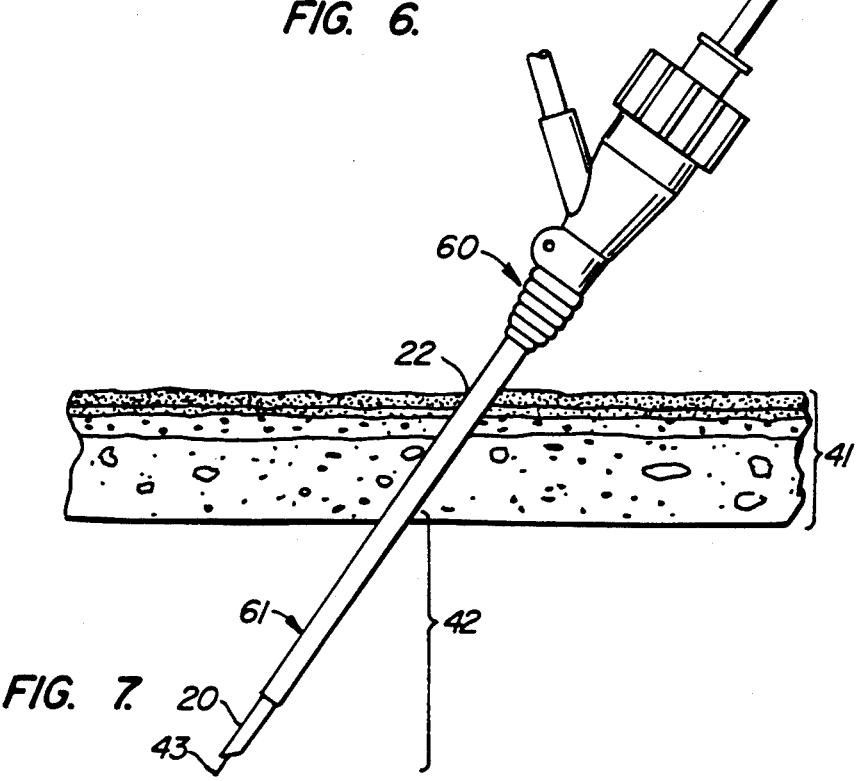
FIG. 7 depicts the use of the percutaneous access device of FIGS. 5 and 6 in positioning a catheter through the skin.

The percutaneous access device 60 comprises an intracorporeal tube 61, a valve housing 62, and a valve cap 64 for optionally compressively sealing two-component valve means 63 within the housing 62. With the inclusion of the normally closed hemostatic valve, the compressive sealing of the anti-bacterial valve is not necessary to prevent air and blood leakage. These components have communicating central bores 66-70 for permitting the insertion and removal of tubular devices such as the catheter 20 (FIGS. 2 and 7).

As illustrated, device 60 includes an inlet side port 72 for blood sampling, infusion, etc., which feeds into housing bore 67. As is shown most clearly in FIG. 5, the bore 67 of the housing 62 includes bore section 73 which is stepped outwardly via tapered conical section 74 to enlarged, threaded outer or distal section 75. The valve cap 64 comprises a tubular section having a threaded outer surface 76 which mates with valve housing threaded section 75 for rotatably attaching the valve cap to the valve housing and removing the valve cap.

Cooperating Overall Structure of Valve Means 63

As alluded to previously, the valve means 63 comprises the inner or proximal duck bill hemostatic sealing valve 81 and the outer or distal anti-bacterial squeegee valve 82. Separating the sealing and anti-bacterial functions has several advantages. The material and the construction of each valve can be optimized to its dominant function. The squeegee valve 82 provides wiping and anti-microbial functions. The sealing valve 81 prevents direct contact of the blood with the anti-bacterial agent in the valve 82, thereby preventing any potential systemic release and patient complications. We should note that valves 81 and 82 assist secondarily in the wiping and sealing functions, respectively. Also, with the inclusion of normally closed, inner valve, the compressive sealing of the outer anti-microbial valve is not necessary to prevent air and blood leakage.

Figure 5:
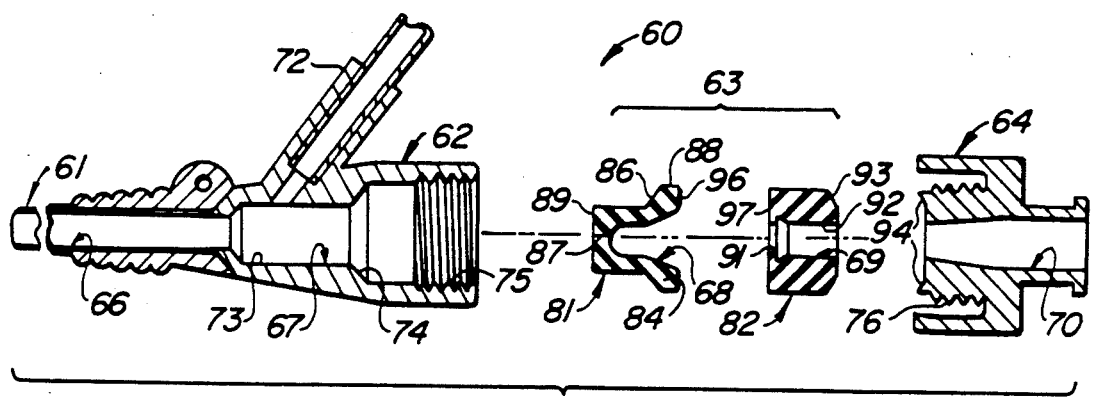
FIG. 5 is an exploded longitudinal sectional view of another embodiment of our percutaneous access device which uses separate sealing and anti-bacterial wiping valves with duck bill lower valve.

Referring further to FIG. 5, the anti-bacterial squeegee valve 82 comprises a generally cylindrical body having stepped bore 69 which itself comprises a relatively small forward section 91 which serves the purpose of an inner O-ring seal and is stepped to a relatively larger outer diameter section 92 which serves the purpose of guiding the catheter and providing the polymer drug reservoir. Tapered conical distal surface 93 mates with the complementary tapered surface 94 of the rotary cap 64. The two valves 81 and 82 mate along complementary-shaped typically flat facing surfaces 96 and 97.

Specific Features of the Anti-Bacterial Squeegee Valve 82

The anti-bacterial squeegee valve 82 (and valve 108, discussed below) preferably comprises a polymer body loaded with an anti-bacterial agent in the polymer so that drug release occurs in the static state, and further that the controlled mechanical compression applied to the valve during use automatically increases (accelerates) the release of the agent. The preferred polymers are polysiloxanes, polyurethanes, and natural rubbers. The preferred anti-bacterial agents are chlorhexidine compounds, phenolic disinfectants, and silver compounds.

Figure 15A:
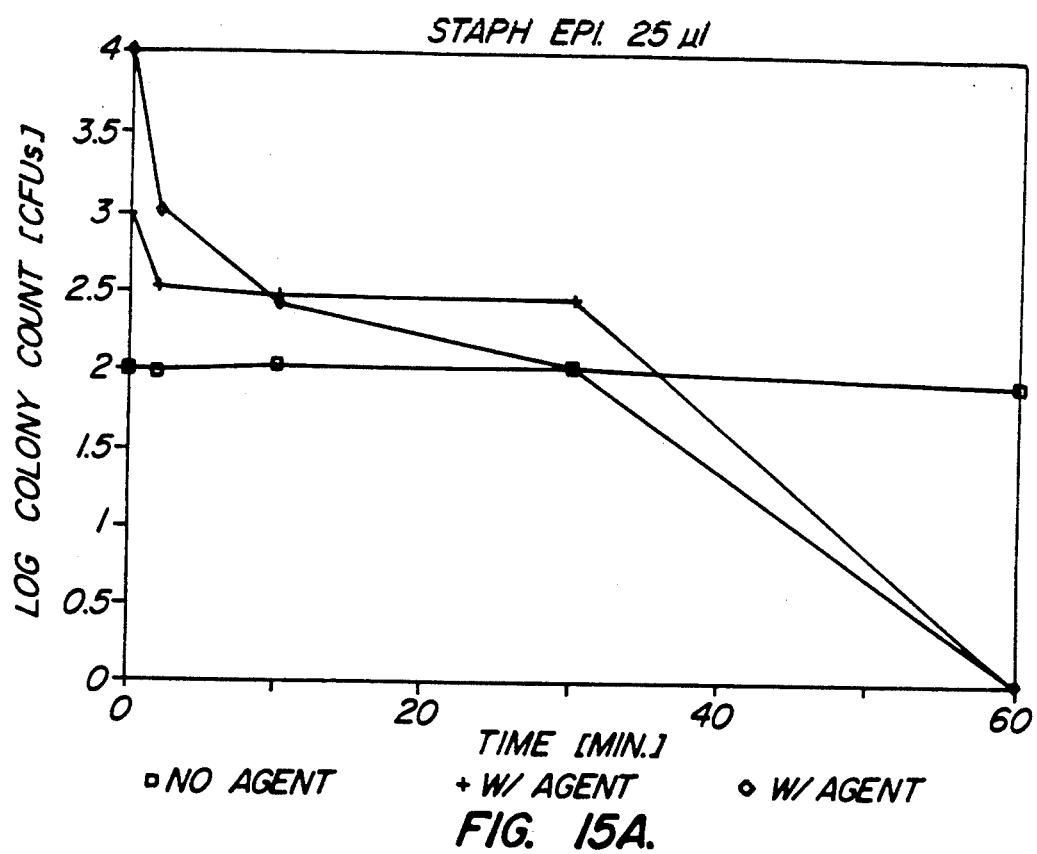
FIGS. 15A and 15B graphically depict the bacterial inactivation properties of the anti-microbial upper valve.
Figure 15B:
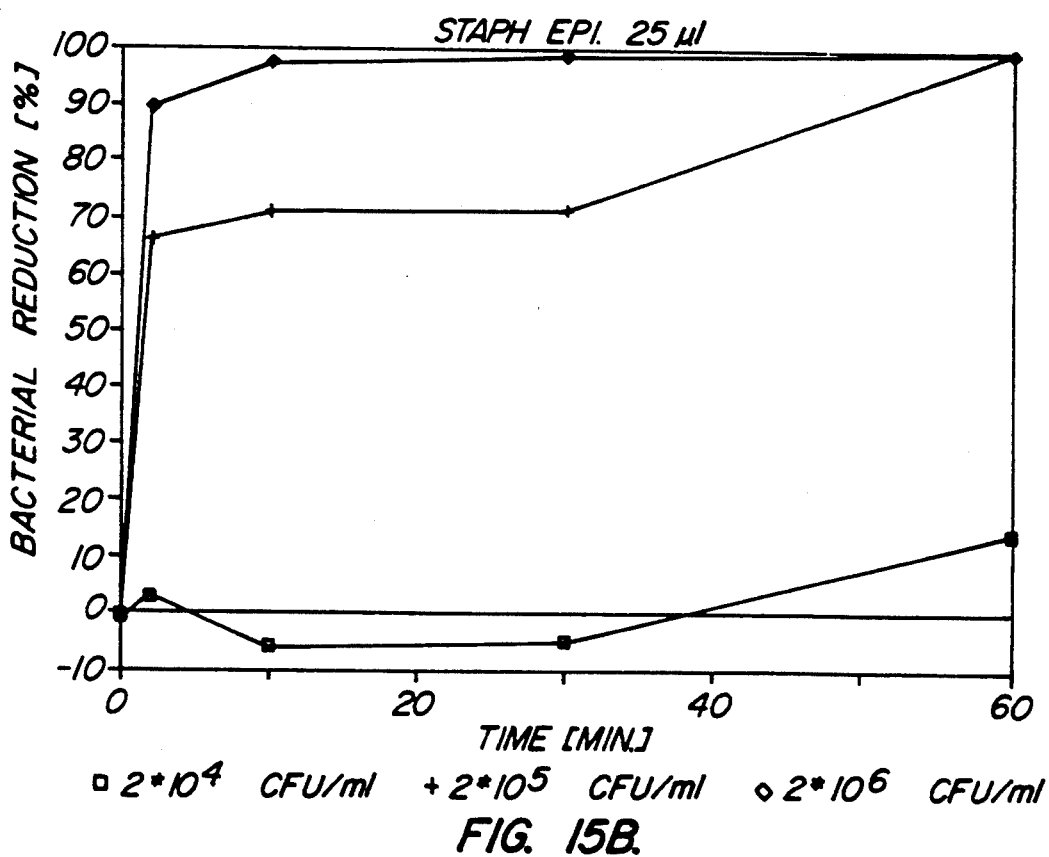

As discussed below, FIGS. 15A and 15B depict the anti-bacterial activity of the squeegee valve in simulated in-vitro bacterial challenge.

Bacterial Challenge of Anti-Bacterial Valve/Squeegee

Staph Epidermidis, ATCC #12228, was grown in an overnight culture of tryptic soy broth (TSB) and various dilutions made. Twenty-five microliters of the innoculum was pippetted onto the anti-bacterial valve of the percutaneous access device, simulating contamination of the valve either by the passage of a contaminated catheter or from inadvertent exposure to contaminated fluids such as sputum.

At various times, five microliters of the innoculum was recovered, the anti-bacterial agent neutralized, and the sample cultured on tryptic soy agar for quantitation of colony forming units (CFUs). Five additional microliters was also removed for quantitation of the anti-microbial agent. A sterile catheter was passed through the valve assembly containing the remaining innoculum into 50 ml of TSB. The TSB samples were incubated and observed for turbidity, indicating bacterial contamination.

| Valve Type | Innoculum Concentration | Exposure Time | CFUs Recovered | Catheter Broth Culture |
|---|---|---|---|---|
| Control (no anti-microbial agent) | 100 CFUs/5 μl | 0 min. | 101 | — |
| | | 2 min. | 97 | positive |
| | | 10 min. | 106 | positive |
| | | 30 min. | 105 | positive |
| | | 60 min. | 86 | positive |
| Test (with agent) | 1,000 CFUs/5 μl | 0 min. | | — |
| | | 2 min. | 337 | positive |
| | | 10 min. | 290 | positive |
| | | 30 min. | 286 | positive |
| | | 60 min. | 0 | sterile |
| Test (with agent) | 10,000 CFUs/5 μl | 0 min. | | — |
| | | 2 min. | 1035 | positive |
| | | 10 min. | 260 | sterile |
| | | 30 min. | 107 | sterile |
| | | 60 min. | 0 | sterile |

Figure 8:
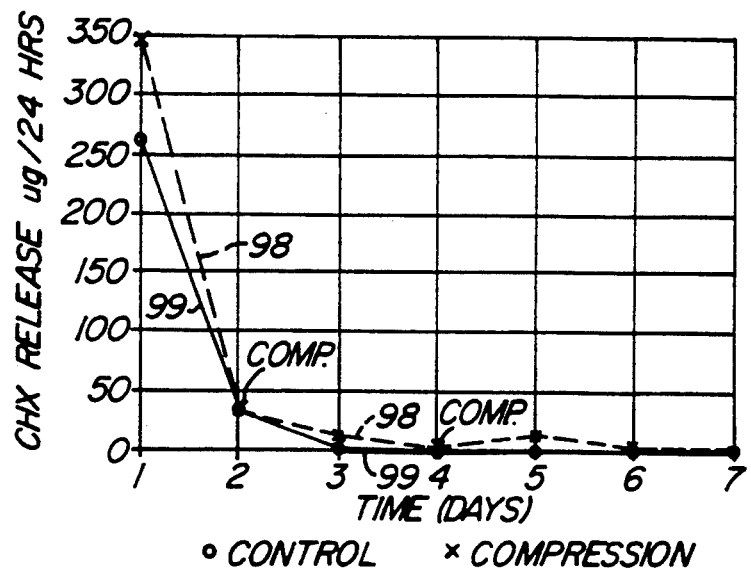
FIGS. 8 and 9 graphically depict the enhanced/accelerated release ("rechargeable release") of the antibacterial agent resulting from mechanical compression of the squeegee valve.
Figure 9:
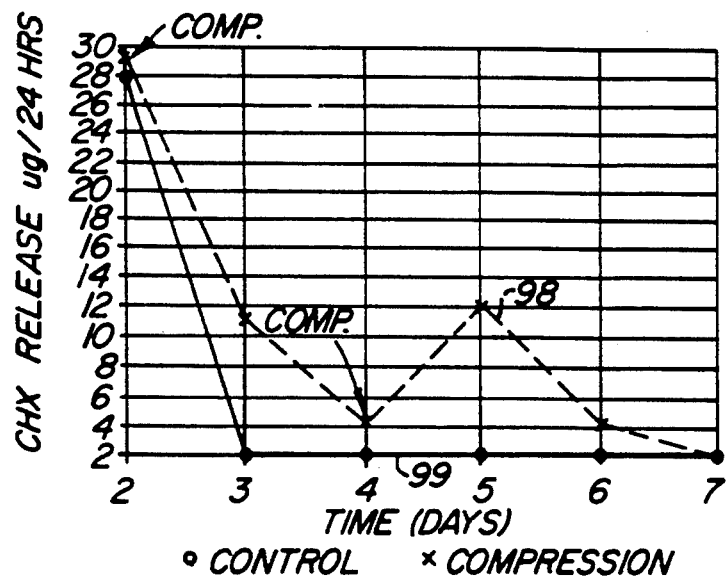

FIGS. 8 and 9 depict the accelerated release characteristics which result from the use of silicone polymer impregnated with chlorhexidine acetate (CHX) anti-bacterial agent. The depicted accelerated compression release was demonstrated using polymer pellets or lozenges in a mechanical fixture, because the geometry of the axial valves 82 and 108 are inconvenient for drug release studies. Thus, although the resulting recharging of the anti-bacterial septum depicted in FIGS. 8 and 9 and discussed below may occur to a smaller degree in the valves 82 and 108 due to surface area/volume considerations, the same accelerated release/recharging characteristics will be present.

In the test, the lozenges of silicone elastomer loaded with the chlorhexidine acetate were placed in 10 cc g water. The chlorhexidine efflux was monitored by optical absorbance at 253 nanometers at 24 hour intervals. At two days and four days, the compression samples were removed and placed in a compression fixture for four hours at 2,000 psi, providing the compression sample data points associated with curve 98 in FIGS. 8 and 9. The control samples were removed from the solution but not compressed, providing the data points associated with control curve 99 in FIGS. 8 and 9. At the end of each compression, both the non-compression control samples and the compression samples were resuspended in fresh water and the chlorhexidine efflux was again monitored. The data points in the figures represent an average of three samples each.

As depicted in FIG. 8 and in particular in FIG. 9 (which expands the ordinate (CHX release) for the time period two to seven days), the CHX release from the non-compression samples decreased after three days to a steady state, equilibrium release of about 2 micrograms per 24 hour period. In contrast, the release from the compression samples increased greatly after each compression. As a result, after two days, the rate of release of CHX from the compression samples was 100 percent to 500-600 percent greater than the rate of release from the control samples. It is particularly noteworthy that the accelerated release effect is greatest once steady state release is reached after three days, just when the additional released drug (500-600 percent increase) is needed most.

Use of the Two-Valve Device 60

Figure 6:
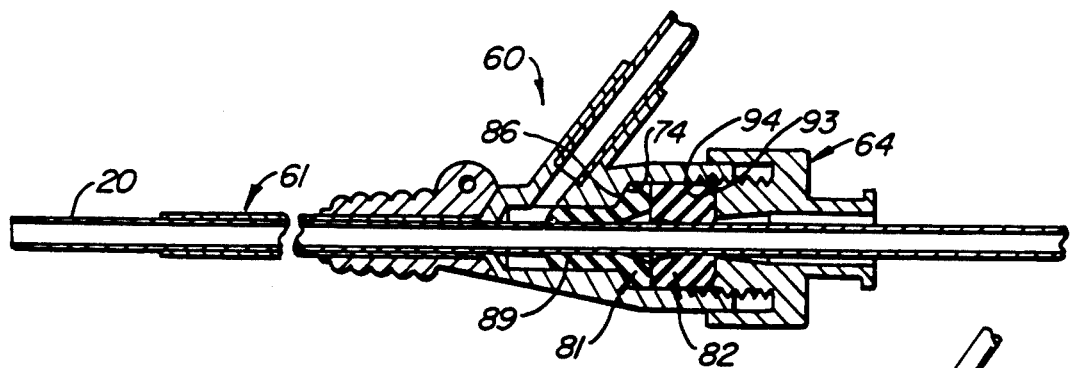
FIG. 6 is a longitudinal sectional view of the percutaneous access device of FIG. 5, as assembled, with a tubular device such as a catheter in place.

The percutaneous access device 60 is assembled and used in generally the same manner as the device 10. Referring to FIGS. 6 and 7, the two valves 81 and 82 comprising the valve means 63 are inserted into the valve housing 62 and the valve cap 64 is threaded onto the housing so that the housing and valve surfaces (including conical surfaces 74 and 94) compressively mate against the corresponding surfaces of the two valves (including conical duck bill surface 86 and conical squeegee valve surface 93), causing valve 81 to seal about the associated catheter or other tubular device and causing the squeegee valve 82 to controllably wipe the tubular device during insertion and/or removal. The device is placed subcutaneously and the catheter 20 is inserted through the device and the valve cap 64 is optionally tightened as needed to secure the catheter 20, and to fix the anti-bacterial barrier provided by valve 82. To remove the catheter 20, the valve cap 64 is unscrewed slightly to loosen engagement of the squeegee valve 82, and the catheter or other tubular device is withdrawn. The anti-bacterial squeegee valve 82 provides anti-bacterial wiping and inactivation of bacteria during insertion and removal of the catheter, and provides a long-lasting anti-bacterial barrier to the introduction of bacteria along the catheter.

2. Device 100: Hemostatic and Air Reflux Sealing Valve and Anti-Bacterial Sealing and Squeegee Valve Construction and Operation of Device 100

Figure 10:
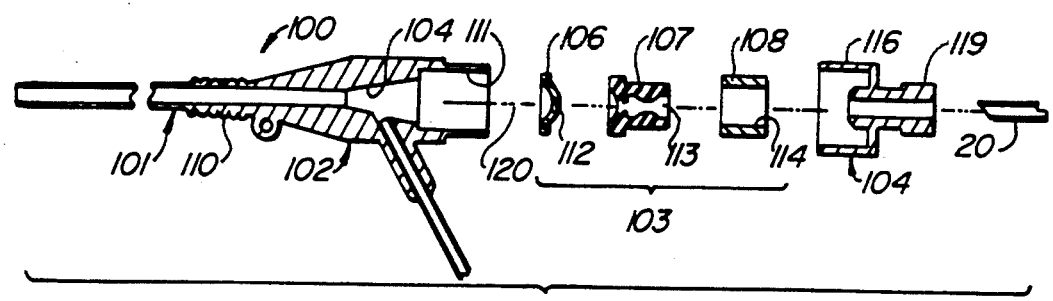
FIG. 10 is an exploded longitudinal sectional view, in the manner of FIGS. 1 and 5, of a presently preferred two-valve embodiment of our percutaneous access device with hemispherical lower valve.

Referring to FIGS. 10–13 and, in particular, to FIG. 10, there is shown a two-valve embodiment 100 of our percutaneous access device which comprises an intracorporeal tube 101; a valve housing or hub 102; valve or plug assembly 103; and a locking bayonet cap 104. The valve assembly 103 comprises an inner or proximal hemispherical valve 106 typically formed of a suitable elastomer such as polysiloxane or natural rubber; a cylindrical, compression-activated, anti-bacterial sealing and squeegee valve 107 formed of polysiloxane elastomer and impregnated with the above-described anti-bacterial agent; and a valve-positioning tube 108 formed of a suitably rigid thermoplastic such as polyethylene or polypropylene. The hub 102 has a stepped bore 109 which includes a large inner diameter distal section 111 for receiving the valve assembly 103, as is perhaps shown most clearly in FIG. 13. The hemispherical valve 106 includes a transverse slit 112 while squeegee valve 107 comprises a large diameter longitudinal hole 113 and tube 108 has a longitudinal hole 114 which provides a close sliding fit over the smaller outer diameter rear section of the stepped valve 107. Locking bayonet cap 104 comprises a cap section 116 having an L-shaped slot 117 shown in FIG. 13 for twist locking onto pin 118 on hub 102. The cap 104 also includes a tubular catheter guide 119. These components are sized so that when the device 100 is assembled, the communicating central bores and slit 112 are aligned along axis 120, thereby permitting insertion and removal of the catheter 20 or other tubular devices.

As discussed above, the diameters of the bores can be chosen so that the percutaneous access device can be used to introduce a number of other elements such as electrical wires and bone pins. Also, the introducer tube 101 can be formed integrally with hub 102 or formed as a separate component which is removable for replacement, sterilization, etc. Typically, the introducer tube 101 is formed of relatively flexible plastic such as polyurethane or PTFE while the hub 102 and bayonet cap 104 are hard plastic such as polycarbonate or PVC, to provide the desired durable locking and compression qualities. When the soft plastic tube 101 is formed integrally with the relatively hard hub 102, a corrugated or ribbed molding 110 may be incorporated for stress relief.

Figure 12:
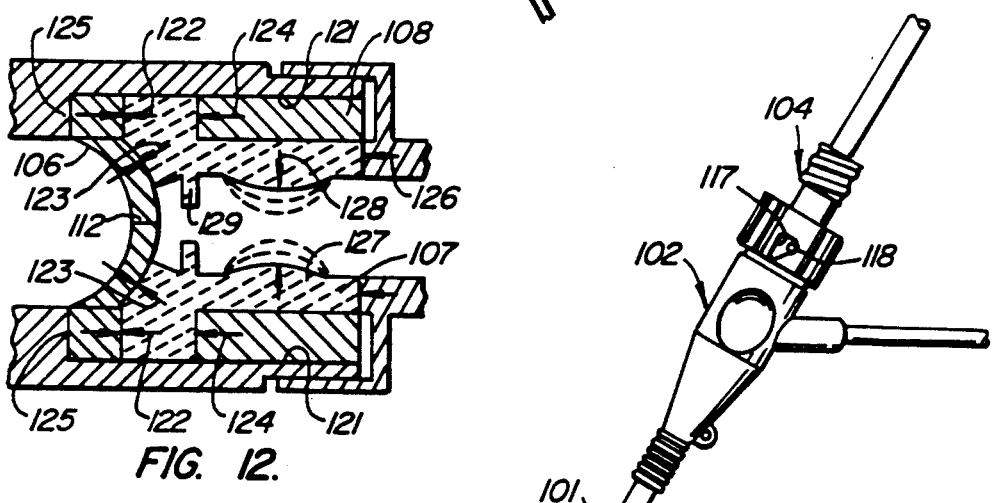
FIG. 12 is an enlarged partial sectional view of the percutaneous access device of FIG. 10, as assembled, depicting the effect of longitudinal compression in reducing the inner bore of the anti-microbial upper valve for improved sealing and catheter wiping.

FIG. 12 is an enlarged illustration of the assembled hub assembly and valve components 103. For assembly, the valves 106 and 107 are inserted into the hub bore 111 and the positioning tube 108 is compressively inserted in abutting relationship against the valve 107 and preferably is bonded to the inside 111 of the hub 101, as indicated at 121, using ultrasonic bonding or other suitable joining techniques. As indicated by the arrows designated 122-124, the compression of the two valves between the hub shoulder 125 and the positioning tube 108 compressively seals the surfaces of the hub, valves and tube, one against the other.

Figure 13:
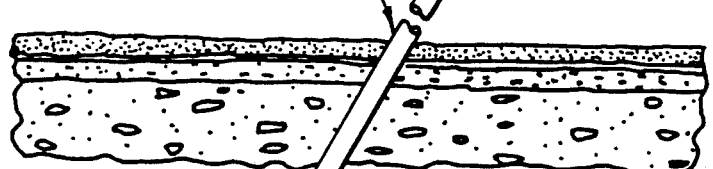
FIG. 13 depicts the use of the percutaneous access device of FIGS. 10-12 in positioning a catheter through the skin.

The catheter 20 is inserted through the locking cap 104 and the hub 102 into the desired subcutaneous position, then the cap 104 is locked onto the hub 102 by first moving the cap slot 117 forward along pin 118 to longitudinally compress the valves 106 and 107, then rotating the cap sideways into the locked position on pin 118 as shown in FIG. 13. As mentioned, longitudinal compression of the cylindrical valve 107 causes the anti-bacterial valve walls 127 to bulge further inwardly as indicated schematically at 128, thus mechanically further sealing the valve against the outer diameter of catheter 20, FIG. 11, and establishing a compressively-enhanced long-lasting anti-bacterial barrier about the circumference of the catheter. The intrinsic O-ring, 129, provides fail-safe sealing regardless of the use of the compression locking cap.

The simple, two-position operation of the cap 104 and hub 102, specifically the fixed, locked closed position illustrated in FIG. 13, limits the longitudinal compression of the valve 107 and thereby prevents over-compression and damage to the catheter.

When cap 104 is unlocked or removed, longitudinal compression is not applied to valve 107, but ring 129 nonetheless lightly engages the outer diameter of the catheter 20 and provides an anti-bacterial wiping or squeegee action when a catheter is removed or inserted.

Hemispherical valve 106 permits easy insertion and removal of the catheter 20 or other tubular device and, when a catheter is not in the hub, closes slit 112 and prevents air reflux into the artery or vein and blood leakage from the artery or vein. (It should be noted that when a catheter is inserted in the hub, valve 106 provides sealing action against air reflux and blood leakage via the bore, but the primary, independently sufficient sealing action is provided by the intrinsic O-ring 129 of the valve 107.)

Figure 14:
FIGS. 14A-14C depict the use of a prior art valve and the associated long-valve stretch dimension.

Referring now primarily to FIG. 12 and FIG. 14, unlike many prior art hemostatic valves 130 which extend inwardly or proximately, i.e., are inwardly convex, our hemispherical valve 106 extends outwardly or distally, i.e., is outwardly convex. The inwardly convex prior art valves provide a good barrier to the outward seepage or leakage of blood but have the potential for air reflux into the associated vein or artery which, as will be readily appreciated, is a more dangerous condition than seepage. Also, and as is indicated sequentially and schematically in FIGS. 14A-14C, as a catheter is removed, the inwardly-oriented prior art valve 30 will on occasion deflect from the full inward facing orientation of FIG. 14A to the outward-facing orientation of FIG. 14C due to frictional contact with the catheter. The resulting long valve stretch resists catheter removal. In contrast, our outwardly-convex valve 106 provides greater resistance to air reflux without overly increasing insertion resistance and permits relatively easier catheter removal due to the reduction in valve stretch, by the contact of the hemisphere valve surface against the surface of the upper anti-microbial valve 107.

Summary of Use and Advantages of Device 100

Figure 11:
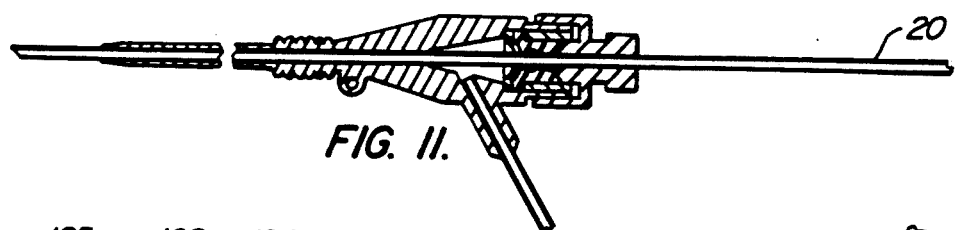
FIG. 11 is a longitudinal sectional view of the percutaneous access device of FIG. 10, as assembled, with a tubular device such as a catheter in place.

As mentioned, the percutaneous access device 100 is used in generally the same manner as devices 10 and 60. Referring initially to FIGS. 11 and 12, with the two valves 106 and 107 sealed within hub 102 by the tube 108, and with cap 104 positioned on but not locked to hub 102, a catheter 20 is threaded through the assembled cap and hub and inserted subcutaneously. See FIG. 13. As mentioned, even without the longitudinal compression which is provided by locking the cap 104, valve ring 129 provides effective anti-bacterial wiping action during insertion and removal of the catheter 20. After the catheter is positioned subcutaneously, the cap 104 is optionally pressed forward and rotated into the locked position, thereby compressively enlarging ring 127 as indicated at 128 and, thus, mechanically securing and sealing the catheter 20 and compressively activating long-term anti-bacterial action. To remove, replace or reposition a catheter, the cap 104 is unlocked and the catheter or other tubular device is withdrawn with anti-bacterial squeegee action and, if desired, the catheter or a new one is inserted through the valve 107, again with the associated squeegee action. After insertion, the cap 104 is locked to reactivate the compressively-enhanced anti-microbial action.

In short, our simple two-valve device 100 separates and individually maximizes the sealing functions using individual valves. The outwardly convex first valve 106 prevents air reflux and leakage when a catheter is absent, and permits easy catheter insertion and removal. The second valve 107 provides mechanical securement and mechanical compression-enhanced anti-bacterial sealing when a catheter is present and anti-bacterial squeegee or wiping action when a catheter is being inserted or removed; and includes a simple, two-position hub lock operation which activates the long-term compression-enhanced anti-bacterial action and at the same time prevents over-compression of and damage to the catheter.

Alternatively, the anti-bacterial valve 107 can be incorporated into the device 100 or other catheter introducers without valve 106 and/or without a compression cap.

Also, the reverse, axially outwardly convex hemispherical valve 106 can be used without the valve 107 and/or without a compression cap. For example, valve 107 can be formed in a non-stepped configuration and of a size to occupy bore 111 without the valve 106 or the positioning tube 107, and the pin 118 can be positioned rearwardly on the hub 102 so that the cap 104 encloses the hub but does not compress the valve 107 when locked. As a result, valve 107 provides anti-bacterial or anti-microbial squeegee wiping action without compressive recharging.

Of course, other, non-bayonet caps could also be used. For example, the previously described threaded caps will provide both a compressively recharged anti-bacterial seal and mechanical securement as well as anti-bacterial squeegee action.

C. Device 130: Preferred Non-Compressive, Multi-Valve Embodiment

Figure 16:
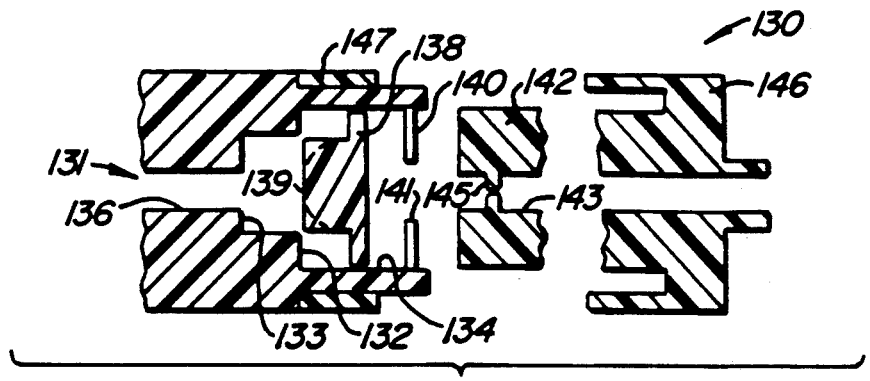
FIG. 16 is an exploded cross-sectional view of a presently preferred non-compression three-valve device.

FIG. 16 depicts a cross-sectional view of a presently preferred non-compressive device 130 which includes two valves and an integral O-ring. Housing bore 131 is stepped at 132 and 133 from large diameter rear/distal section 134 to a small diameter front/proximal section 136 which is of approximately the same diameter as the catheter or other device 20. The valve arrangement comprises a flexible duck-bill valve 138, which has a transverse slit 139, and mates with the steps 132 and 133; an intermediate washer 140, typically having an inner diameter 141 larger than the diameter of the associated catheter or other device 20; and an anti-bacterial impregnated cylinder 142 having a bore 143 with an intrinsic O-ring section 145. Cap 146 is screwed onto the threaded upper end of the housing. Cylindrical outer ring 147 is of a length to allow the cap 146 to provide a snug, slightly compressive sealed mating among the two valve members and the washer and the housing, while preventing over-tightening and possible damage to the components, including the catheter or other inserted device 20. Washer 140 separates the valves 138 and 142 and helps prevent distortion of the valve 138 during assembly or cap adjustment. In this so-called non-compressive device, the intrinsic O-ring 145 within valve 142 provides the anti-bacterial squeegee wiping function similar to part 129 in FIG. 12.

Considered as a whole, the sealing arrangement comprises the outer or distal valve 142 incorporating an anti-microbial drug release and wiping function and the proximal valve 138 which together allow aseptic introduction and repositioning, while maintaining a gas and fluid seal during introduction and repositioning. The intrinsic O-ring 145 of the distal seal 142 prevents breach of the gas fluid seal when the proximal valve 138 is breached during introduction of the catheter.

The foregoing description of various preferred and alternative embodiments of the invention is presented for purposes of illustration and description. It is not intended to be exhaustive or to limit the invention to the precise form disclosed. Obviously, many modifications and variations are possible in light of the disclosure contained herein. The preferred embodiment was chosen and described in order to best explain the principles of the invention and its practical application to thereby enable others of skill in the art to best utilize the invention and the various disclosed embodiments as well as the various modifications that will be derived by those of skill in the art. It is thus intended that the scope of the invention be limited only by the claims.

What is claimed is:

1. In a percutaneous access device having an intracorporeal adapted for aseptic leak-proof insertion therethrough of a tubular device such as a catheter, comprising the improvement: valve means having a bore therein for receiving a tubular device, the valve means comprising a first valve proximally located to the point of insertion of said tubular device into body tissue, adapted for hemostatic sealing against the outside of the tubular device and a second valve impregnated with an antibacterial agent distally located to said point of insertion of said tubular device into body tissue, and adapted for sealing against the outside of the tubular device when said device is positioned within the bore of the valve means and wiping the tubular device during movement thereof along the bore of the valve means; and a valve housing having a bore therein for receiving the tubular device and the valve means.

2. A percutaneous access device adapted for aseptic leak-roof insertion therethrough of a tubular device such as a catheter, comprising:
 a tubular valve housing having first and second opposite ends and having a bore having at least an enlarged section extending from the first end to the second end thereof for receiving both a tubular body and valve means positioned over said tubular body;
 tubular valve means having a bore therein fitting over said tubular body and comprising two interactive valves; the first valve comprising a duck bill valve having first and second ends; the first end of the duck bill valve being tapered; and the second valve having first and second ends, the first end of the second valve being configured for complementarily mating with the second end of the first valve and the second end of the second valve being tapered; the second valve further being formed of resilient polymer material selectively impregnated with an anti-microbial agent for providing compressive recharging of anti-microbial activity; and
 a tubular valve cap having threads mating with the valve housing for releasably attaching the cap onto the second end of the valve housing and including a tapered section mating with the second tapered end of the second valve, for selectively compressing the second valve between the cap and the valve housing so that selection of the mounting position of the valve cap on the valve housing and the associated compression of the second valve effects at least one of resiliently sealing the valve about the tubular device, insertion of the tubular device through the valve, anti-bacterial wiping action along the device during insertion and providing a rechargeable anti-bacterial barrier on the tubular device.

3. A percutaneous access device adapted for aseptic insertion therethrough of a tubular device such as a catheter, and further adapted for resealing upon removal of said tubular device therefrom, comprising:
 a tubular valve means formed of resilient polymer material selectively impregnated with an antimicrobial agent for providing compressive recharging of anti-microbial activity, the valve means further including an axial opening and having a tapered end;

a tubular valve housing having first and second opposite ends, including an intracorporeal tube attached at the first end thereof, and having a bore extending from the first end to the second end for receiving the tubular value means therein, the bore including a tapered section for mating with said tapered end of the tubular valve means; and a tubular valve cap including means for releasably attaching the cap to the second end of the valve housing and selected positions thereon, for selectively compressing the tubular valve means between the cap and the valve housing, so that section of the position of the tubular cap on the valve housing is effective to provide for resilient sealing of the tubular valve means about the tubular device, insertion of the tubular device therethrough, rechargeable anti-bacterial wiping action along the tubular device during insertion, a rechargeable anti-bacterial barrier on the device upon insertion; and for selectively compressing said tubular valve means between said cap and said valve housing upon removal of said tubular device so that selection of the position of said tubular cap on said valve housing is effective to seal with axial opening in said tubular valve means.

4. A device according to claim 3 wherein said valve means includes said tapered end as a first end and further includes a second tapered end opposite to said first end; and said tubular valve cap includes a tapered section mating with said second tapered end of said valve means.

5. The percutaneous access device of claim 3 or 4 wherein the intracorporeal tube and the valve housing are separate elements, mutually adapted for attachable assembly.

6. The percutaneous access device of claim 3 or 4 wherein the intracorporeal tube and the valve housing comprise a single element.

7. The percutaneous access device of claim 3 or 4 wherein the intracorporeal tube includes a raised annulus of tissue in-growth promoting material for promoting a tissue seal and mechanical attachment to the skin.

8. A percutaneous access device adapted for aseptic leak-proof insertion therethrough of a tubular body such as a catheter comprising:

a tubular valve housing having first and second opposite ends and including a bore having at least an enlarged section extending from the first end to the second end thereof for receiving both the tubular body and valve means positioned over said tubular body;

tubular valve means comprising a cylindrical valve and an O-ring for wiping said tubular body during insertion and removal thereof, at least the O-ring being selectively impregnated with an anti-microbial agent; and a valve cap, said cap and said housing having cooperating means for attaching said cap to said housing to secure the cylindrical valve within the housing to effect anti-microbial wiping action along the tubular body during insertion and removal thereof.

9. The percutaneous access device of claim 8, wherein the O-ring is an integral, internal, radially inwardly extending section of the cylindrical valve body.

10. The percutaneous access device of claim 9, the cooperating attachment means selectively positioning the valve cap along the housing to thereby adjustably compress the tubular valve means between the valve cap and the valve housing for effecting compression-enhanced anti-microbial sealing of the tubular valve means about the tubular body.

11. The percutaneous access device of claim 10, the tubular valve means further including, in front of the cylindrical valve, a valve member comprising a peripheral annular section and an inner, rearwardly-convex hemispherical body section within the peripheral section having a transverse slit therein; the forward end of the cylindrical valve being configured such that the cylindrical valve and the valve member mate snugly one against the other; both the cylindrical valve body and the valve member being formed of resilient polymer material.

12. The percutaneous access device of claim 8, wherein the O-ring is separate from the cylindrical valve.

13. The percutaneous access device of claim 8, further comprising a duck bill valve positioned in front of the cylindrical valve which incorporates the O-ring; each of the duck bill valve, and the cylindrical valve having front and rear surfaces configured for mating snugly against the adjacent valve surfaces or intermediate spurs or washers; the duck bill valve and cylindrical valve being formed of resilient polymer material.

14. A percutaneous access device adapted for aseptic leak-proof insertion therethrough of a tubular body such as a catheter comprising:

a tubular valve housing having first and second opposite ends and having a bore having at least an enlarged section extending from the first end to the second end thereof for receiving both the tubular body and valve means positioned over said tubular body;

tubular valve means fitting within the bore of said tubular valve housing and over said tubular body and comprising two valve members: a first valve member comprising a peripheral annular section and an inner, outwardly-convex hemispherical body section within the peripheral section and having a transverse slit therein; a second valve member comprising a cylindrical valve body having an internal radially-inwardly protruding ring section for wiping said tubular body during insertion and removal thereof and being sized for mating against the peripheral section of the first valve body; and means for compressively sealing the valve bodies together against a shoulder formed within said bore of the tubular valve housing; the first and second valve members being formed of resilient polymer material and the second valve member being selectively impregnated with an anti-microbial agent; and a tubular valve cap, said cap and said housing having cooperating locking means for attaching said cap to said housing and selectively compressing the second and first valve members between the cap and the valve housing so that mounting the valve cap on the valve housing and associated compression of the second valve member effects a compression-enhanced anti-microbial seal of the second valve member about the tubular device and whereby said first valve provides a barrier against liquid leakage and air reflux when said tubular device is not present.

15. A percutaneous access device adapted for aseptic leak-proof insertion therethrough of a tubular body such as a catheter, comprising:

a tubular valve housing having first and second opposite ends and having a bore having at least an enlarged section stepped to a smaller section at the first end, the bore extending from the first end to the second end thereof for receiving both the tubular body and valve means positioned over said tubular body;

tubular valve means fitting within the bore of said tubular valve housing and over said tubular body and comprising: a front duck bill valve having a transverse slit for sealingly and slidably receiving said tubular body and having a front side configured for snugly mating against the stepped section of the bore; a rear cylindrical valve having an inner bore slidably receiving said tubular body, the inner bore thereof incorporating an intrinsic O-ring having an internal diameter configured to effect wiping action along said tubular body during insertion and removal thereof; the valves being formed of elastomeric material; and the rear wiping valve being selectively impregnated with anti-microbial agent.

16. The percutaneous access device of claim 15, further comprising a spacer washer between the front duck bill valve and the rear cylindrical wiping valve.

17. A percutaneous access device adapted for aseptic leak-proof insertion therethrough of a tubular body such as a catheter, comprising:

a tubular valve housing having first and second opposite ends and having a bore having at least an enlarged section stepped to a smaller section at the first end, the bore extending from the first end to the second end thereof for receiving both the tubular body and valve means positioned over said tubular body;

tubular valve means fitting within the bore of said tubular valve housing and over said tubular body and comprising: a front duck bill valve having a transverse slit for sealingly and slidably receiving said tubular body and having a front side configured for snugly mating against the stepped section of the bore; a rear cylindrical valve having an inner bore slidably receiving said tubular body; an O-ring intermediate the front duck bill valve and the rear cylindrical valve and having a hole therein of lesser diameter than the bore of the cylindrical wiping valve for effecting wiping action along said tubular body during insertion and removal thereof; the valves being formed of elastomeric material; and the rear cylindrical wiping valve being selectively impregnated with anti-microbial agent.

18. The percutaneous access device of any of claims 2, 3, 8, 14, 15 and 17, wherein the valve means is silicone and the anti-microbial agent is chlorhexidine.

19. The percutaneous access device of any of claims 2, 14, 15 and 17, further comprising an intracorporeal tube and wherein the intracorporeal tube and the valve housing are separate elements, mutually adapted for attachable assembly.

20. The percutaneous access device of claim 19, wherein the intracorporeal tube includes a raised annulus of tissue in-growth promoting material for promoting a tissue seal and mechanical attachment to the skin.

21. The percutaneous access device of any of claims 2, 8, 14, 15 and 17, further comprising an intracorporeal tube and wherein the intracorporeal tube and the valve housing comprise an integral component.

22. The percutaneous access device of claim 21, wherein the intracorporeal tube includes a raised annulus of tissue in-growth promoting material for promoting a tissue seal and mechanical attachment to the skin.

23. The percutaneous access device of claim 21, wherein the intracorporeal tube and the valve housing are joined by a ribbed pressure relief member.

* * * * *

UNITED STATES PATENT AND TRADEMARK OFFICE
CERTIFICATE OF CORRECTION

PATENT NO. : 5,059,186

DATED : October 22, 1991

INVENTOR(S) : Ronald K. Yamamoto, et al.

It is certified that error appears in the above-identified patent and that said Letters Patent is hereby corrected as shown below:

Column 4, line 2, "(Fig. which facilitates..." should read --(Fig. 1) which facilitates...--.

Signed and Sealed this

Twenty-third Day of March, 1993

Attest:

STEPHEN G. KUNIN

*Attesting Officer*          Acting Commissioner of Patents and Trademarks

UNITED STATES PATENT AND TRADEMARK OFFICE
CERTIFICATE OF CORRECTION

PATENT NO. : 5,059,186

DATED : October 22, 1991

INVENTOR(S) : Yamamoto; Conston; Bootman

It is certified that error appears in the above-identified patent and that said Letters Patent is hereby corrected as shown below:

Col. 12, line 27: "leak-roof" should read --leak proof--.

Signed and Sealed this

Eighteenth Day of May, 1993

Attest:

MICHAEL K. KIRK

Attesting Officer

Acting Commissioner of Patents and Trademarks

UNITED STATES PATENT AND TRADEMARK OFFICE
CERTIFICATE OF CORRECTION

PATENT NO. : 5,059,186
DATED : October 22, 1991
INVENTOR(S) : Yamamoto; Conston; Bootman It is certified that error appears in the above-indentified patent and that said Letters Patent is hereby corrected as shown below:

In Column 12, line 10: "poreal adapted" should be
-- poreal tube adapted --

Signed and Sealed this

Eighth Day of June, 1993

Attest:

MICHAEL K. KIRK

Attesting Officer

Acting Commissioner of Patents and Trademarks